United States Patent
Park et al.

(10) Patent No.: US 7,049,109 B2
(45) Date of Patent: May 23, 2006

(54) **METHOD OF PRODUCING 1,2-PROPANEDIOL USING *KLEBSIELLA PNEUMONIAE***

(75) Inventors: Young Hoon Park, Seongnam (KR); Jin Su Chung, Yongin (KR); Kwang Myung Cho, Icheon (KR); Seong Uk Kang, Yongin (KR); Hye Won Um, Suwon (KR)

(73) Assignee: CJ Corp. (KR)

( * ) Notice: Subject to any disclaimer, the term of this patent is extended or adjusted under 35 U.S.C. 154(b) by 0 days.

(21) Appl. No.: 10/815,882

(22) Filed: Mar. 31, 2004

(65) Prior Publication Data

US 2004/0197881 A1   Oct. 7, 2004

(30) Foreign Application Priority Data

Apr. 2, 2003   (KR) .................... 10-2003-0020734

(51) Int. Cl.
*C12P 7/04* (2006.01)
(52) U.S. Cl. .................. 435/157; 435/155; 435/132; 435/41; 435/166; 435/170; 435/243; 435/852
(58) Field of Classification Search ............... 435/168, 435/132, 41, 252.1, 852, 243, 166, 155, 170, 435/157
See application file for complete search history.

(56) References Cited

U.S. PATENT DOCUMENTS 6,303,352 B1 * 10/2001 Cameron et al. ........... 435/158

OTHER PUBLICATIONS

"Microbial formation, biotechnological production and applications of 1,2-propanediol"; Authors: G. N. Bennett and K.-Y. San; Appl Microbiol Biotechnol, 55:; Springer-Verlag 2001; pp. 1-9.

"Fermentation Mechanism of Fucose and Rhamnose in *Salmonella typhimurium* and *Klebsiella pneumoniae*"; Authors: Josefa Badia, Joaquim Ros and Juan Aguilar; Journal of Bacteriology, vol. 161, No. 1; American Society for Microbiology, Jan. 1985; pp. 435-437.

* cited by examiner

*Primary Examiner*—Leon B. Lankford, Jr.
*Assistant Examiner*—Allison M. Ford
(74) *Attorney, Agent, or Firm*—Cantor Colburn LLP

(57) ABSTRACT

A method of producing 1,2-propandiol is provided. The method includes incubating *Klebsiella pneumoniae* in a medium containing 10–30 g/L of a sugar carbon source excluding 6-deoxyhexose, in aerobic conditions; and separating 1,2-propandiol from the cultures. Using the method, 1,2-propandiol can be produced with a high yield by incubating *Klebsiella pneumoniae* in a medium containing a cheaper sugar carbon source.

7 Claims, No Drawings

METHOD OF PRODUCING 1,2-PROPANEDIOL USING *KLEBSIELLA PNEUMONIAE*

BACKGROUND OF THE INVENTION

This application claims the priority of Korean Patent Application No. 2003-20734, filed on Apr. 2, 2003, in the Korean Intellectual Property Office, the disclosure of which is incorporated herein in its entirety by reference.

1. Field of the Invention

The present invention relates to a method of producing 1,2-propanediol using *Klebsiela pneumoniae*.

2. Description of the Related Art 1,2-propanediol is a very useful intermediate used in the production of optically active compounds including medicines, agricultural chemicals, antifreezes, and physiologically active agents.

According to a known chemically synthetic pathway for the production of 1,2-propandiol, 1,2-propandiol can be produced by the hydrogenation of propylene oxide derived from propylene. When producing 1,2-propandiol through this chemically synthetic pathway, excess water is necessary to suppress the production of polyglycol. In addition, the production of propylene oxide, which is involved in the production of 1,2-propandiol, requires costly chemical catalysts and leads to a large amount of byproducts, such as chlorohydrine and chroline, causing environmental contamination.

In a known biological method of producing 1,2-propandiol, L-rhamnose and L-fucose are utilized to produce by using *E. coli* and other microorganisms. However, L-rhamnose and L-fucose are very expensive and using these materials is uneconomical. Cameron et al. discloses a method of producing 1,2-propandiol from glucose using *Thermoanaerobacterium thermosaccharolyticum* HG-8 (ATCC 31960) (Biotechnol. Prog. 2001, Vol. 17, pp. 52~56). U.S. Pat. No. 6,303,352 issued to Cameron et al. discloses a method of producing 1,2-propandiol from glucose using recombinant *E. coli*.

However, all of the above-listed conventional methods utilize strains excluding *Klebsiella pneumoniae*. It is known that, when *Klebsiella pneumoniae* is incubated in a medium containing 6-deoxyhexose, such as rhamnose and fucose, in anaerobic conditions, the yield of 1,2-propandiol increases. It is also known that 1,2-propanediol can be produced from glucose using *Klebsiella pneumoniae* in both aerobic and anaerobic conditions. However, the yield of 1,2-propandiol from glucose is too low for commercialization (Juan Aguilar et al., J. Bact. January 1985, 435~437).

There has been intensive research into a highly efficient method of producing 1,2-propandiol from a non-sugar carbon source, not expensive sugar carbon sources, such as 6-deoxyhexose, including rhamnose and fucose, using *Klebsiella pneumoniae*. As a result, the inventors of the present invention found that 1,2-propandiol can be produced with a high yield when *Klebsiella pneumoniae* is incubated in a medium containing a large amount of a common sugar carbon source, such as glucose, in aerobic conditions.

SUMMARY OF THE INVENTION

The present invention provides a highly efficient method of producing 1,2-propandiol by incubating *Klebsiella pneumoniae* in a medium containing a common sugar carbon source in aerobic conditions.

According to an aspect of the present invention, there is provided a method of producing 1,2-propandiol, the method comprising: incubating *Klebsiella pneumoniae* in a medium containing 10–30 g/L of a sugar carbon source excluding 6-deoxyhexose, in an aerobic conditions; and (b) separating 1,2-propandiol from the cultures.

DETAILED DESCRIPTION OF THE INVENTION

A highly efficient method of producing 1,2-propandiol according to an embodiment of the present invention includes: incubating *Klebsiella pneumoniae* in a medium containing a sugar carbon source excluding 6-deoxyhexose, in an aerobic conditions; and separating 1,2-propandiol from the cultures. *Klebsiella pneumoniae* may be a strain of an accession number of ATCC 25955. 1,2-propandiol may be separated from the cultures using a common method, for example, ion exchange chromatography, high performance liquid chromatography (HPLC), and crystallization.

Alternatively, the medium may further contain an organic acid as an intermediate metabolite. The organic acid intermediate metabolite may be, but are not limited to, selected from the group consisting of pyruvate, fumarate, citrate, and succinate. For batch incubation, all of the organic acid intermediate metabolite may be added to the medium at the initial stage of incubation, while in fed-bacth incubation or continuous incubation, the organic acid intermediate metabolite may be added continuously or intermittently throughout the incubation process.

According to the present invention, the sugar carbon source includes, but is not limited to, commonly available sugars, such as selected from the group consisting of arabinose, fructose, galactose, glucose, lactose, maltose, sucrose, xylose, and a combination of the foregoing sugars. In other word, the sugar carbon source used in the present invention excludes 6-deoxyhexose, such as rhamnose and fucose. A preferred example of the sugar carbon source is glucose.

In the present invention, it is preferable that the content of sugar carbon source in the medium is maintained in an excess for a predetermined period in terms of the cell metabolization rate. For example, the amount of the sugar carbon source may be in a range of 10–30 g/L, and preferably 10–20 g/L. The amount of the sugar carbon source may be in a range of, most preferably, 10–30 g/L as glucose. If the amount of the sugar carbon source is greater than 30 g/L or less than 10 g/L, the yield of 1,2-propandiol is low.

In an embodiment of the present invention, the medium may contain 5–15 g of $Na_2HP_4$, 3–8 g of $KH_2PO_4$, 0.5–4 g of $NH_4Cl$, 2–7 g of NaCl, 3–10 g of a yeast extract, 0.1–3 mmol of $MgSO_4$, and 10–30 g of glucose per liter.

The incubation of *Klebsiella pneumoniae* may be performed at a temperature of 30–37° C. and pH 5–8. Oxygen may be supplied during the incubation in such an amount as to give an aerobic condition. For example, oxygen may be supplied by means of commonly known oxygen supplying methods, for example, by shaking the incubator, agitation using an agitator, or air injection. Oxygen may be supplied at 0–1 vvm.

The present invention will be described in greater detail with reference to the following examples. The following examples are for illustrative purposes and are not intended to limit the scope of the invention.

EXAMPLE 1

Incubation of *Klebsiella pneumoniae* for Production of 1,2-propandiol

*Klebsiella pneumoniae* of Accession No. ATCC 25955 was cultured in a medium having the following composition of Table 1 below for 1,2-propanediol production. The 1,2-propandiol producing medium had a pH of 6.8.

TABLE 1

Composition of 1,2-propandiol production medium

| Component | Amount per liter |
|---|---|
| $Na_2HPO_4$ | 10 g |
| $KH_2PO_4$ | 5 g |
| $NH_4Cl$ | 2 g |
| NaCl | 5 g |
| Yeast Extract | 1 g |
| $MgSO_4$ | 1 mmol |
| Glucose | 20 g |

50 mL of the medium was poured into a 250-mL baffled flask and sterilized at 121° C. for 15 minutes under pressure. Glucose to be added to the medium was also separately sterilized. The sterilized medium and Glucose were thoroughly mixed to obtain the 1,2-propandiol producing medium.

*Klebsiella pneumoniae* of ATCC 25955 pre-cultured on a nutrient agar (NA) plate was inoculated in 20 mL of LB broth and incubated at 200 rpm for 24 hours. 1 mL of the cultured broth was inoculated into the medium for 1,2-propandiol production and incubated at 37° C. and 200 rpm for 24 hours.

EXAMPLE 2

Quantification of 1,2-propanediol in the Cultures

The amount of 1,2-propanediol in the cultures obtained in Example 1 was measured. 1 mL of the cultures were harvested into 1.5-mL tubes and centrifuged at 12,000 rpm for 10 minutes. The supernatants from the centrifugation were transferred into empty tubes and 5-fold diluted with sterilized distilled water. The amount of 1,2-propandiol in each of the diluted samples was measured using high performance liquid chromatography (HPLC).

The results are shown in Table 2 below. As shown in Table 2, the produced amount of 1,2-propandiol is 3.838 g/L, which is larger than that of 1,2-propandiol obtained by using a conventional method (Juan Aguilar et al., J. Bact. January 1985, 435~437).

TABLE 2

The amount of 1,2-propanediol in the cultures

| Strain | Residual glucose (g/l) | The amount of 1,2-propandiol (g/l) | The amount of biomass ($OD_{600}$) |
|---|---|---|---|
| *Klebsiella pneumoniae* (ATCC 25955) | 0 | 3.838 | 6.54 |

EXAMPLE 3

Yield Improvement by Addition of Organic Acid Intermediate Metabolite

The effect of adding fumarate as an organic acid intermediate metabolite on the yield of 1,2-propandiol was investigated. To this end, 1 mM/L of fumarate was added to the 1,2-propandiol producing medium prepared in Example 1. *Klebsiella pneumoniae*) of ATCC 25955 was incubated in the fumarate-containing medium in the same conditions as in Example 1 and the amount of 1,2-propandiol produced was measured using the same method as used in Example 2.

The results are shown in Table 3 below. As shown in Table 3, the yield of 2,3-propandiol is markedly increased compared to the result from Example 2, in which no fumarate was added to the 1,2-propandiol producing medium prepared in Example 1.

TABLE 3

The amount of 1,2-propandiol produced using fumarate-containing medium

| Addition of fumarate | Residual glucose (g/l) | The amount of 1,2-propandiol (g/l) | The amount of biomass ($OD_{600}$) |
|---|---|---|---|
| X | 0 | 3.695 | 6.54 |
| ○ | 0 | 5.988 | 8.05 |

Based on the above-described results from the examples, it is confirmed that 1,2-propandiol can be produced with a higher yield than using conventional methods by incubating *Klebsiella pneumoniae* in a medium containing a sugar carbon source in excess amount in aerobic conditions. In addition, the yield of 1,2-propandiol can be further improved when an organic acid as an intermediate metabolite is added to the 1,2-propandiol producing medium.

As described above, in a method of producing 1,2-propandiol according to the present invention, 1,2-propandiol can be produced with a higher yield using a medium containing a cheaper common sugar carbon source and *Klebsiella pneumoniae*. The yield of 1,2-propandiol can be further improved when an organic acid as an intermediate metabolite is added to the medium.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of producing 1,2-propandiol, the method comprising:
   (a) incubating *Klebsiella pneumoniae* in a medium containing 10–30 g/L of a sugar carbon source excluding 6-deoxyhexose, in aerobic conditions; and
   (b) separating 1,2-propandiol from the cultures.

2. The method of claim 1, wherein the medium includes an organic acid intermediate metabolite.

3. The method of claim 2, wherein the organic acid intermediate metabolite is selected from the group consisting of pyruvate, fumarate, citrate, and succinate.

4. The method of any one of claims 1 through 3, wherein the sugar carbon source is selected from the group consisting of arabinose, fructose, galactose, glucose, lactose, maltose, sucrose, xylose, and a combination of the foregoing sugars.

5. The method of any one of claim 1 through 3, wherein the medium contains 5–15 g of $Na_2HPO_4$, 3–8 g of $KH_2PO_4$, 0.5–4 g of $NH_4Cl$, 2–7 of NaCl, 3–10 g of yeast extract, 0.1–3 mmol of $MgSO_4$, and 10–30 g of glucose per liter.

6. The method of any one of claims 1 through 3, wherein the incubating of *Klebsiella pneumoniae* in the medium is performed at pH 5–8 and a temperature of 30–37° C.

7. The method of any one of claims 1 through 3, wherein oxygen is supplied at 0–1 vvm during the incubation.

* * * * *